(12) United States Patent
Clark

(10) Patent No.: US 12,396,736 B2
(45) Date of Patent: Aug. 26, 2025

(54) ADHESIVE PAD AND HEMOSTASIS SYSTEM

(71) Applicant: Forge Medical, Inc., Morrisville, NC (US)

(72) Inventor: Timothy W. I. Clark, Philadelphia, PA (US)

(73) Assignee: Forge Medical, Inc., Morrisville, NC (US)

( * ) Notice: Subject to any disclaimer, the term of this patent is extended or adjusted under 35 U.S.C. 154(b) by 464 days.

(21) Appl. No.: 18/075,061

(22) Filed: Dec. 5, 2022

(65) Prior Publication Data
US 2023/0103229 A1   Mar. 30, 2023

Related U.S. Application Data

(63) Continuation of application No. 15/203,049, filed on Jul. 6, 2016, now Pat. No. 11,517,323.

(51) Int. Cl.
*A61B 17/132* (2006.01)
*A61B 17/00* (2006.01)
*A61B 17/08* (2006.01)
*A61B 17/12* (2006.01)

(52) U.S. Cl.
CPC ........ *A61B 17/132* (2013.01); *A61B 17/0057* (2013.01); *A61B 17/085* (2013.01); *A61B 2017/0065* (2013.01); *A61B 2017/12004* (2013.01)

(58) Field of Classification Search
CPC . A61B 17/132; A61B 17/0057; A61B 17/085; A61B 2017/0065; A61B 2017/12004
See application file for complete search history.

(56) References Cited

U.S. PATENT DOCUMENTS

| | | | |
|---|---|---|---|
| 3,086,530 A | 4/1963 | Groom |
| 5,263,965 A | 11/1993 | Roth |
| 5,728,120 A | 3/1998 | Shani et al. |
| 6,068,646 A | 5/2000 | Lam |

(Continued)

FOREIGN PATENT DOCUMENTS

EP          67622 A1     12/1982

OTHER PUBLICATIONS

U.S. Appl. No. 15/203,049, filed Jul. 6, 2016, Pending, U.S. Pat. No. 11,517,323, Dec. 6, 2022.

*Primary Examiner* — Tan-Uyen T Ho
*Assistant Examiner* — Cherie M Poland
(74) *Attorney, Agent, or Firm* — Christopher J. Knors; Moore & Van Allen PLLC

(57) ABSTRACT

An adhesive pad for use with a hemostasis device comprising a footplate having a top surface and a receiving device positioned on the footplate, the adhesive pad comprising: (1) a flexible backing layer having a bottom surface, a central portion having an opening, a first side portion, and a second side portion; (2) an adhesive layer applied to the bottom surface of the backing layer; and (3) a release layer removably secured to the adhesive layer. The opening in the central portion of the backing layer is sized to fit the receiving device of the hemostasis device, and the adhesive layer applied to the bottom surface of the first and second side portions of the backing layer is configured to adhere to and extend beyond the top surface of the footplate.

11 Claims, 6 Drawing Sheets

(56) References Cited

U.S. PATENT DOCUMENTS

| | | | |
|---|---|---|---|
| 6,316,686 B1 | 11/2001 | Byrd | |
| 6,332,879 B1 | 12/2001 | Nielsen et al. | |
| 7,780,612 B2 | 8/2010 | Ross | |
| 11,517,323 B2* | 12/2022 | Clark | A61B 17/132 |
| 2002/0058893 A1 | 5/2002 | Vesey | |
| 2003/0028214 A1 | 2/2003 | Benz et al. | |
| 2004/0068290 A1 | 4/2004 | Bates et al. | |
| 2005/0085757 A1 | 4/2005 | Santanello | |
| 2007/0282239 A1 | 12/2007 | Bates et al. | |
| 2008/0269659 A1 | 10/2008 | Bergin et al. | |
| 2009/0171192 A1 | 7/2009 | Patrick et al. | |
| 2009/0281565 A1 | 11/2009 | Mcneese | |
| 2010/0152770 A1 | 6/2010 | Spencer | |
| 2010/0217202 A1 | 8/2010 | Clark | |
| 2011/0196417 A1* | 8/2011 | Clark | A61F 5/32 606/201 |
| 2012/0191128 A1 | 7/2012 | Teeslink et al. | |
| 2013/0237943 A1 | 9/2013 | Erland | |
| 2018/0008280 A1* | 1/2018 | Clark | A61B 17/132 |

\* cited by examiner

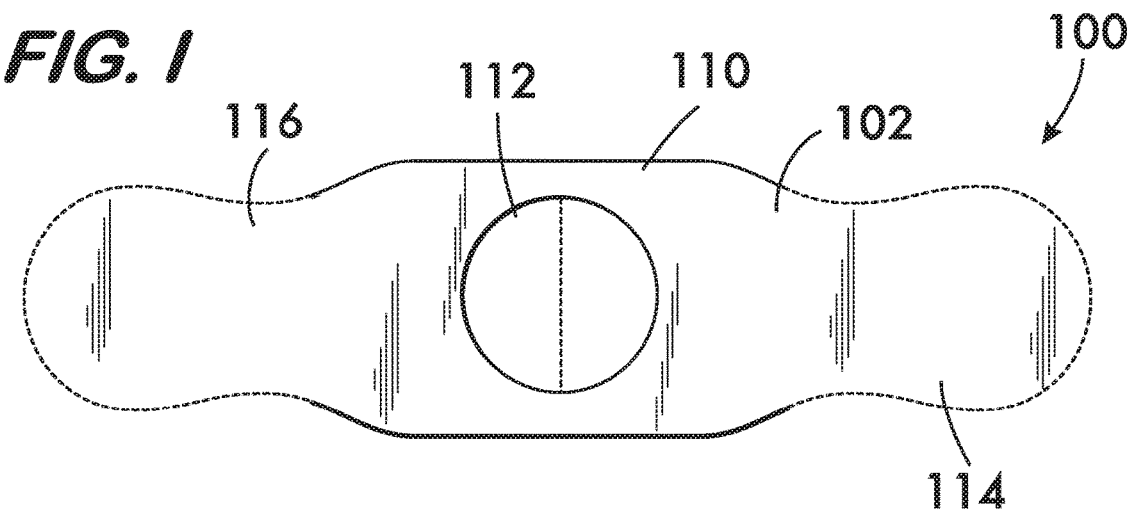
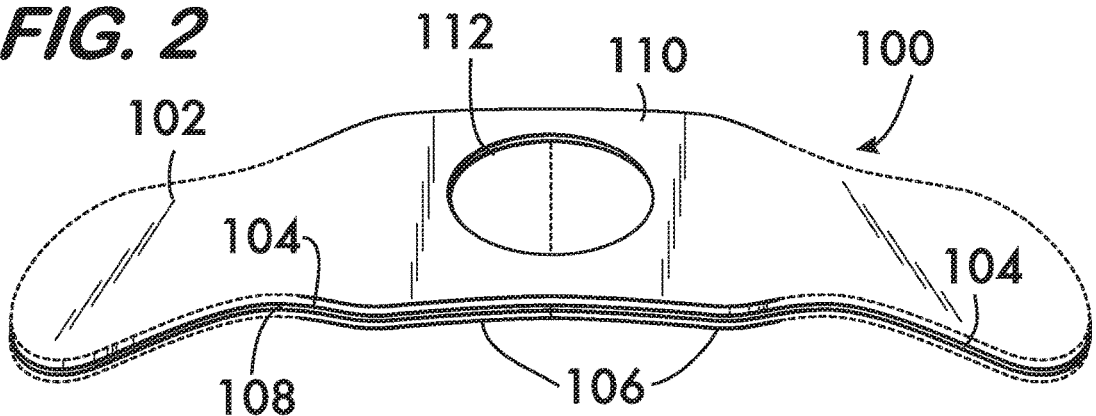
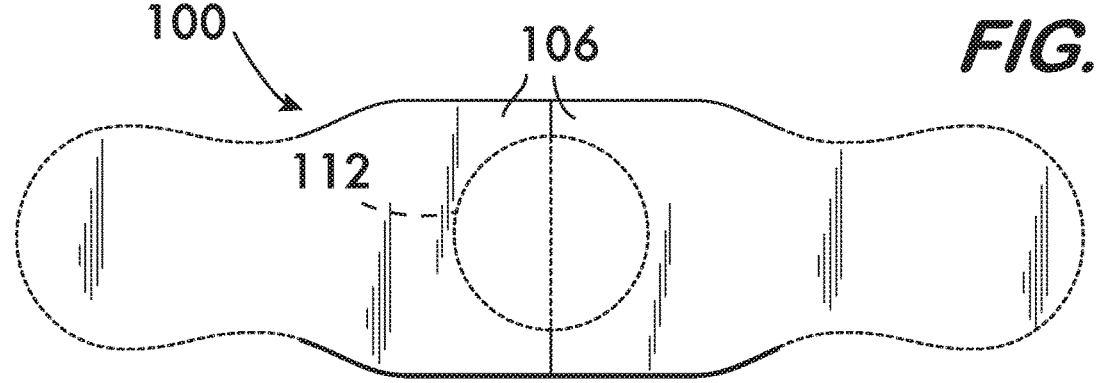
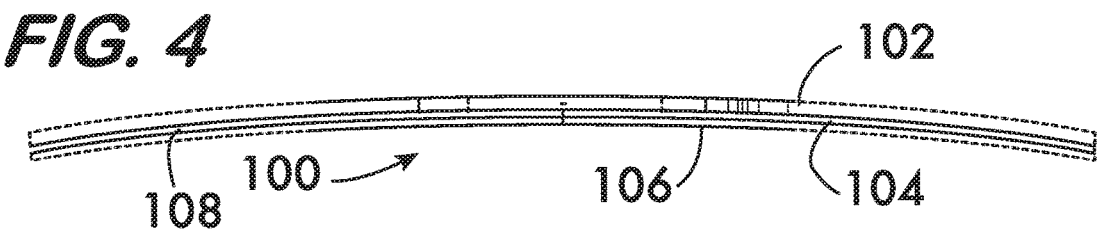

ADHESIVE PAD AND HEMOSTASIS SYSTEM

CROSS-REFERENCE TO RELATED APPLICATIONS

This application is a continuation of U.S. application Ser. No. 15/203,049, filed Jul. 6, 2016, the entirety of which is incorporated herein by reference.

BACKGROUND

The present disclosure relates to an improved adhesive attachment system for devices that adhere to a patient's skin at a vascular access site and apply a compressive force to the puncture site to achieve hemostasis.

There are many devices and procedures currently employed in the medical field for achieving hemostasis at a percutaneous vascular access site resulting, for example, from a transradial cardiac catheterization procedure.

Among such prior art devices and procedures are, for example: a non-woven sponge manually applied directly to the site of the bleeding at the puncture site; band-type devices tightened around the arm of the patient and possessing an inflatable balloon over the blood vessel; and notch-shaped compression pad tightened around the arm of the patient much like an electrical tie.

Each of these prior art devices and procedures require extensive interaction with a patient by a clinician. For example, a non-woven sponge requires the clinician apply pressure to the puncture site until hemostasis is achieved. Similarly, band-shaped compression device requires the clinician to use both hands to wrap the device around the arm (or leg) or a patient and inflate the compressive balloon using an air-filled syringe such that the pressure is applied appropriately to the puncture site. None of these prior art devices provides the clinician with a device that can be applied with a single hand in a manner that allows the clinician to simultaneously remove the vascular access sheath so that hemostasis is achieved.

Improving on these prior art devices and procedures, the VasoStat™ hemostasis device has been developed. The VasoStat™ hemostasis device is configured to apply a compressive force to a patient's skin at the site of a percutaneous vascular access. This device comprises a footplate, a receiving device positioned on the footplate, a plunger positioned within the receiving device and configured to move therethrough, and motion restricting means interposed between the receiving device and the plunger, the motion restricting means configured such that as the plunger moves toward the skin movement of the plunger away from the skin is restricted until the restricting means are released. So configured, this hemostasis device permits single-handed operation allowing the clinician to quickly and efficiently apply the hemostasis device to the puncture site.

The VasoStat™ hemostasis device employs adhesive pads that are applied to the bottom of the footplate. In operation, these pads secure the device to the patient's skin and enable precise alignment of the device over the intended area of vascular compression. In order for the device to achieve a secure adhesion, the pads must have an adhesive force greater than the compressive force applied on the puncture site by the plunger. Thus, the compressive force that may be applied to a puncture site is limited by the surface area of the bottom of the footplate and by the strength of the adhesive used on the pads. If adhesive pads cover the entire surface area of the bottom of the footplate, the application of higher compressive forces can only be achieved by using stronger adhesives. The use of stronger adhesives, however, increases the likelihood that the removal of the device may cause injury or undue discomfort to the patient. Accordingly, there is a need for an attachment system for such hemostasis devices that permits the application of a wider range of compressive forces at a puncture site.

SUMMARY

One aspect of the present invention is an adhesive pad for a hemostasis device that has a footplate, a receiving device positioned in the footplate, and a plunger positioned within the receiving device and configured to move therethrough and apply a compressive force to a patient's skin at a puncture site to assist in hemostasis. The adhesive pad comprises a flexible backing layer, an adhesive layer, and a release liner. The flexible backing layer has a bottom surface, a central portion having an opening, a first side portion, and a second side portion. The adhesive layer is applied to the bottom surface of the backing layer, and the release liner is removably secured to the adhesive layer. The opening in the central portion of the backing layer is sized to fit the receiving device of the hemostasis device. The first and second side portions of the backing layer are configured to overlie and adhere to the footplate of the hemostasis device and to the patient's skin about the footplate.

Another aspect of the present invention is a hemostasis system for adhering to a patient's skin and applying a compressive force to a puncture site, the system comprising a hemostasis device and an adhesive pad. The hemostasis device has a footplate, a receiving device positioned on the footplate, a plunger positioned within the receiving device and configured to move therethrough, and a plurality of motion restricting components interposed between the receiving device and the plunger. The adhesive pad has a flexible backing layer with a bottom surface, a top surface, a first side portion, and a second side portion, and a central portion, an adhesive layer applied to the bottom surface of the backing layer, and a release liner removably secured to the adhesive layer. The central portion of the backing layer of the adhesive pad has an opening sized to fit the receiving device of the hemostasis device, and the first side portion and the second side portion of the backing layer of the adhesive pad are configured to overlie and adhere to the footplate of the hemostasis device and to the patient's skin about the footplate.

Another aspect of the present invention is a method for applying a compressive force to a patient's skin at a puncture site, the method comprising the steps of placing a hemostasis device on the patient's skin at the puncture site, adhesively anchoring an adhesive pad to the hemostasis device and to the patient's skin proximal to the puncture site, and applying a compressive force to the puncture site.

The hemostasis device employed in the present method comprises a footplate, a receiving device positioned on the footplate, a plunger positioned within the receiving device and configured to move therethrough, and a plurality of motion restricting components interposed between the receiving device and the plunger. In practicing the present method, the such hemostasis device is placed on a patient's skin proximal to the puncture site, the plunger is advanced through the receiving device until it applies a compressive force to the puncture site, and the plurality of motion restricting components are engaged to restrict reverse movement of the plunger through the receiving device.

The adhesive pad employed in the present method comprises a flexible backing layer with a bottom surface having an adhesive layer applied thereto, a first side portion, and a second side portion, and a central portion having an opening sized to fit the receiving device of the hemostasis device, wherein at least the first side portion and the second side portion of the backing layer of the adhesive pad overlie and adhere to the footplate of the hemostasis device and to the patient's skin about the footplate.

BRIEF DESCRIPTION OF THE DRAWINGS

Referring now to the drawings, in which like numerals represent like parts in the several views:

FIG. 1 illustrates a top view of an exemplary embodiment of an adhesive pad for a hemostasis device.

FIG. 2 illustrates a perspective view of the adhesive pad of FIG. 1.

FIG. 3 illustrates a bottom view of the adhesive pad of FIG. 1.

FIG. 4 illustrates a side view of the adhesive pad of FIG. 1.

DETAILED DESCRIPTION

Figure 5:
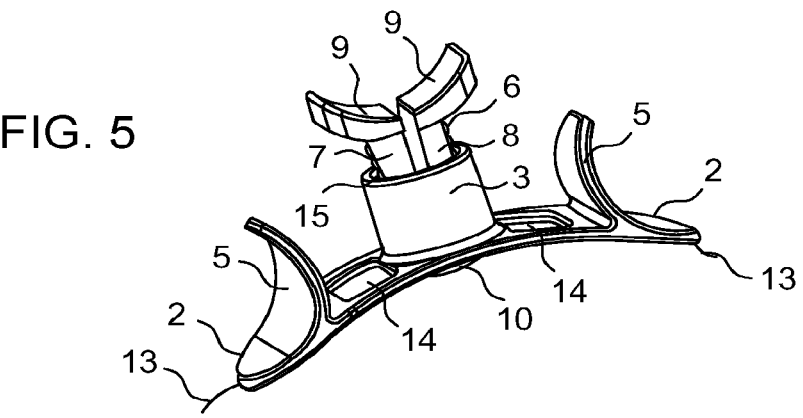
FIG. 5 illustrates an exemplary embodiment of a hemostasis device for use with an adhesive pad according to the present invention.

One aspect of the present invention relates to an adhesive pad for a hemostasis device configured to apply a compressive force to a puncture site on a patient's skin. The hemostasis device is configured such that a clinician may adhere the device to a patient's skin, apply pressure directly to the puncture site using a mechanical plunger, and leave the hemostasis device adhered to the patient's skin until hemostasis is achieved. The hemostasis device may be sized and configured such that it may be used on a patient's forearm, upper arm, head, chest, back, thigh, lower leg, or any other body part. As discussed herein, the hemostasis device is applied to a puncture site resulting from a medical procedure such as, for example, a cardiac catheterization procedure performed through the radial artery; however, the hemostasis device as discussed herein may be applied to any type of puncture site where hemostasis is desired. For example, the hemostasis device described herein may be applied to a wound resulting from an abrasion, incision, laceration, avulsion, amputation, or any other wound where hemostasis is desired. It should be understood that use of the term "puncture site" herein includes punctures resulting from a medical procedure as well as all such types of wounds.

As shown in the embodiment illustrated in FIGS. 1-4, the adhesive pad 100 comprises a flexible backing layer 102, an adhesive layer 104, and a release layer 106. The flexible backing layer 102 has a bottom surface 108, a central portion 110 having an opening 112, a first side portion 114, and a second side portion 116. The adhesive layer 104 is applied to the bottom surface 108 of the backing layer 102, and the release layer 106 is removably secured to the adhesive layer 104. The opening 112 in the central portion 110 of the backing layer 102 is sized to fit over a hemostasis device configured similarly to the hemostasis devices shown in FIGS. 5-10. Such hemostasis devices have a footplate, a receiving device positioned in the footplate, and a plunger positioned within the receiving device and configured to move therethrough and apply a compressive force to a patient's skin at a puncture site. The first and second side portions 114 and 116 of the backing layer 102 are configured to overlie and adhere to the footplate of such hemostasis devices and to the patient's skin about the footplate.

The backing layer 102 is the main structural component of adhesive pad 100. The backing layer 102 may comprise paper, woven or unwoven fibers, flexible foam, or plastic film. In embodiments in which the backing layer 102 is flexible foam, the foam may be formed from various elastomer materials such as polyester or polyether polyurethane foams, styrene-butadiene foams, and certain rubber-based foams. In embodiments in which the backing layer 102 is a plastic film, the film may be formed from various polymers including polyethylene, polypropylene, polyurethane, polyester, poly(ethylene-vinyl acetate), and poly(vinyl chloride). The backing layer 102 may comprise a unitary layer or a combination of layers of materials. For multilayer backing layers, the layers may comprise the same or different materials.

The backing layer 102 bears the adhesive layer 104 on its bottom surface 108 and, in operation, is overlaid on the VasoStat™ hemostasis device or similarly configured hemostasis devices, and is adhesively secured to both the top of the footplate of such devices and to the patient's skin about the footplate. The adhesive pad 100 is sized to provide greater contact area with a patient's skin as compared with the adhesive pads disposed on the footplate of the hemostasis device. As a result, the adhesive pad 100 provides greater adhesive strength for a given adhesive than the adhesive pads disposed on the footplate of the hemostasis device. Thus, for applications in which high compressive forces are required, or if only a weak adhesive is appropriate for the patient or the puncture site, the adhesive system of the present invention—the combination of the adhesive pad of the present invention with the VasoStat™ hemostasis device or a similarly configured hemostasis device—provides enhanced adhesion to the patient's skin that cannot be achieved by the hemostasis device alone. Further, use of the adhesive pad of the present invention permits the application of hemostasis devices without adhesive pads disposed on the bottom surface of the footplate.

The backing layer 102 may also be provided in a variety of shapes. In one embodiment, the backing layer 102 comprises an elongated strip in which the central portion 110 is wider than the two side portions 114 and 116. In another embodiment, the backing layer 102 comprises an elongated strip in which the central portion 110 and the two side portions 114 and 116 have approximately equal widths. In yet another embodiment, the backing layer 102 comprises an elongated strip in which the central portion 110 is narrower than the two side portions 114 and 116. In still other embodiments, the backing layer 102 has an elliptical or circular shape. For embodiments in which the backing layer 102 has an elliptical or circular shape, the first and second side portions 114 and 116 can be regarded as any pair of complimentary semi-elliptical or semi-circular portions.

The adhesive layer 104 provides the adhesion between the backing layer 102 of the adhesive pad 100 and both the top surface of the footplate of the hemostasis device and the patient's skin about the footplate. Any pharmaceutically acceptable adhesive which provides adhesion to a patient's skin that is releasable without significant injury to the patient may be used as the adhesive layer 104. Examples of such suitable adhesives include pressure-sensitive adhesives which do not require solvent, water, or heat to activate the adhesive. Such pressure-sensitive adhesives may comprise acrylates, butyl rubber, ethylene-vinyl acetate, natural rubber, nitriles, silicone rubbers, dimethylsiloxane, isobutylene, urethanes, styrene block copolymers, styrene-butadiene-styrene, styrene-ethylene/butylene-styrene, styrene-ethylene/propylene, styrene-isoprene-styrene, and vinyl ethers.

The release layer 106 covers the adhesive layer 104 and is removed prior to use to expose the adhesive layer 104 prior to application to a patient's skin. Materials suitable for use as the release layer 106 are well-known in the art and include paper and plastic films. In embodiments utilizing a paper release layer, the paper may be coated. In one embodiment, the release layer 106 may comprise a unitary structure. In another embodiment, the release layer 106 may comprise plurality of discrete sections. The release layer 106 may also have an opening coincident with the opening 112 in the central portion 110 of the adhesive pad 100. Alternatively, the release layer 106 may cover a portion or all of the opening 112 in the central portion 110 of the adhesive pad 100.

Exemplary hemostasis devices suitable for use with the adhesive pad of the present invention are shown in FIGS. 5-11B. As shown in FIGS. 5-9, an exemplary hemostasis device suitable for use with the adhesive pad of the present invention may comprise a footplate 2, a receiving device such as cylinder 3 positioned on the footplate 2, a plunger 4 and, optionally, one or more stabilizing means such as one or more curved arms 5 on the footplate 2. The footplate 2 may be made from a flexible material such that the contour of the footplate is capable of adjusting to various areas of the body of a patient having different curvatures. Also, it should be noted that the receiving device is shown as cylindrical by way of example only. Additional cross-sectional shapes may be used such as a rectangle, square, oval, or other geometric shape that allows the receiving device to accept the plunger 4 and permit movement therethrough.

The engagement of the plunger 4 within the cylinder 3 provides for one-directional movement of the plunger 4 with respect to the cylinder 3 such as, for example, by use of a ratcheting mechanism. In one embodiment, one or more racks 6 positioned on the plunger 4 may engage a pawl 15 positioned in cylinder 3 in such manner as to limit plunger 4 to movement downwardly in cylinder 3. In other words, plunger 4 may be forced downwardly toward the puncture site, but is restrained from upward movement in the cylinder 3 by the combination and position of the one or more racks 6 and the internally positioned pawl 15 resulting in a ratcheting in the cylinder 3. In another embodiment, one or more racks 6 on the cylinder 3 may engage a pawl positioned on plunger 4 in such manner as to limit plunger 4 to movement downwardly in cylinder 3. In yet another embodiment, one or more racks 6 on the plunger 4 may engage corresponding racks 16 positioned in cylinder 3 in such manner as to limit plunger 4 to movement downwardly in cylinder 3.

As shown in the embodiments represented in FIGS. 5-9, an upper portion of the plunger 4 may be bifurcated whereby, due to the resilience of the material from which the plunger 4 is made, to force the bifurcations 7 and 8 outwardly against the interior of the cylinder 3, thereby to force the external ratchets 6 on plunger 4 into engagement with the internal ratchets in cylinder 3. As discussed above, this arrangement restrains the plunger 4 from upward movement through the cylinder 3.

The bifurcated portions 7 and 8 at the top of the plunger 4 may be, at their extreme upper ends, arcuate shaped 9, and are adapted to be engaged by a clinician when the hemostasis device 1 is operated. For example, the clinician may engage the top of the plunger 4 with their finger, thumb, palm, or other body part that allows the clinician to assert a downward pressure on the plunger.

The bottom of the plunger 4 may include a compression surface 10 having a compression pad 11 adhered thereto. The compression pad 11 may have a pro-coagulant coating such as calcium alginate, oxidized regenerated cellulose, seaweed extracts, a pro-coagulant polymer, another pro-coagulant coating, or combinations of two or more of these. The compression pad 11 may also have an antimicrobial coating such as silver or chlorhexidine.

One or more pads 12, with adhesive surfaces on both faces thereof, may be applied to the bottom of the footplate 2 such that, during operation, the pads adhere to the skin 13 of the patient when the hemostasis device 1 is in use thereby assisting in securing the footplate 2 to the patient's skin when in use. The size of the pads 12 may be determined relative to the pressure being applied by the hemostasis device 1 to puncture site and/or the part of the body to which the hemostasis device 1 is being applied. The size of the pads 12 may also be determined relative to the type of adhesive used on the pads 12. For example, the adhesive force of the pads 12 should be greater than the compressive force applied to the puncture site by the plunger 4. Typical temporary medical adhesives may be used such that when hemostasis is achieved, the hemostasis device 1 is easily removed.

Figure 6:
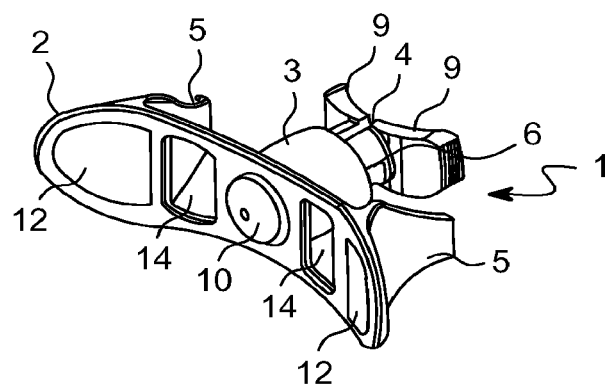
FIG. 6 illustrates the hemostasis device of FIG. 5 showing a plunger in an internally ratcheted cylinder prior to use.
Figure 7:
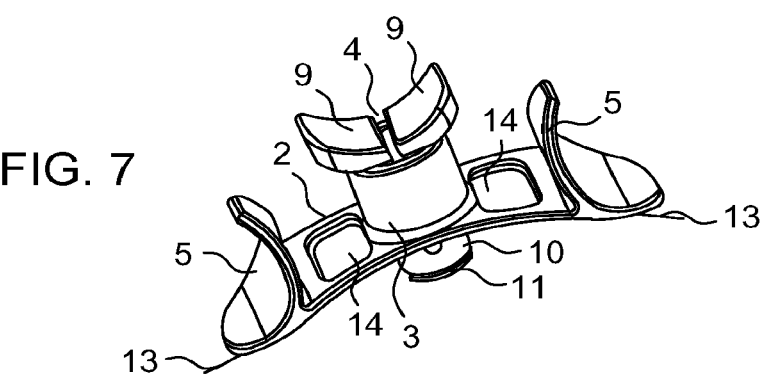
FIG. 7 illustrates the hemostasis device of FIG. 5, showing the plunger fully advanced in the cylinder against a puncture site.

As shown in FIGS. 5-7, additional features such as curved arms 5 may be included on footplate 2. For example, the curved arms 5 may be engaged by the thumb and middle finger of the clinician when the hemostasis device 1 is in use. Alternatively, the curved arms 5 may be engaged by the index and middle fingers of the clinician when the hemostasis device 1 is in use. Either method of operation provides a single-handed operation style allowing the clinician to quickly and efficiently apply the hemostasis device 1.

As shown in FIGS. 5-9, the footplate 2 may also be provided with apertures 14 configured and positioned to allow the clinician to observe the position of the rounded portion 10 of the plunger 4 and the compression pad 11 relative to the puncture site to assure that the hemostasis device 1 is properly positioned over the puncture site.

Figure 9:
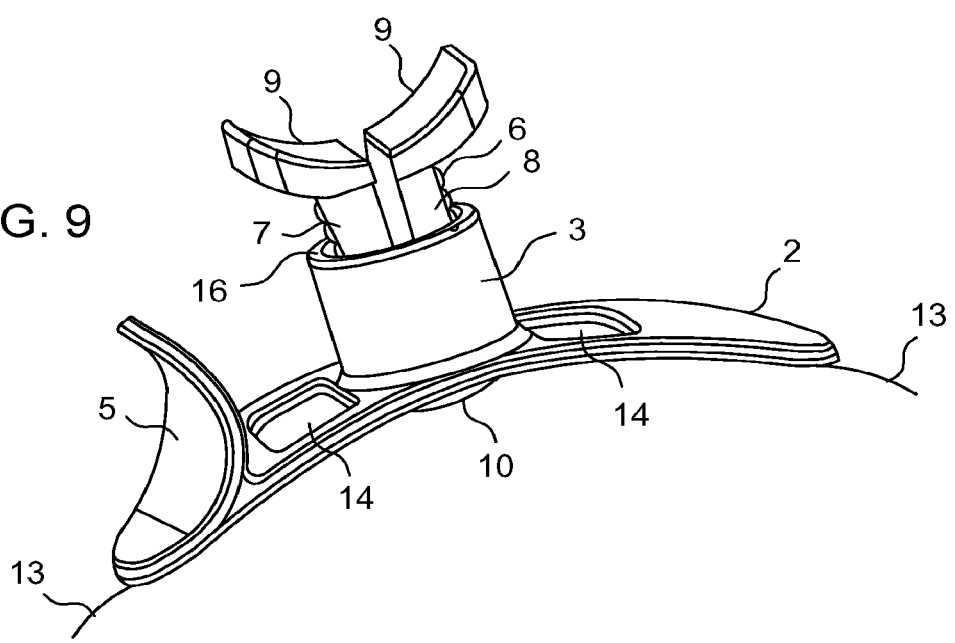
FIG. 9 illustrates a third exemplary embodiment of a hemostasis device for use with an adhesive pad according to the present invention.
Figure 10:
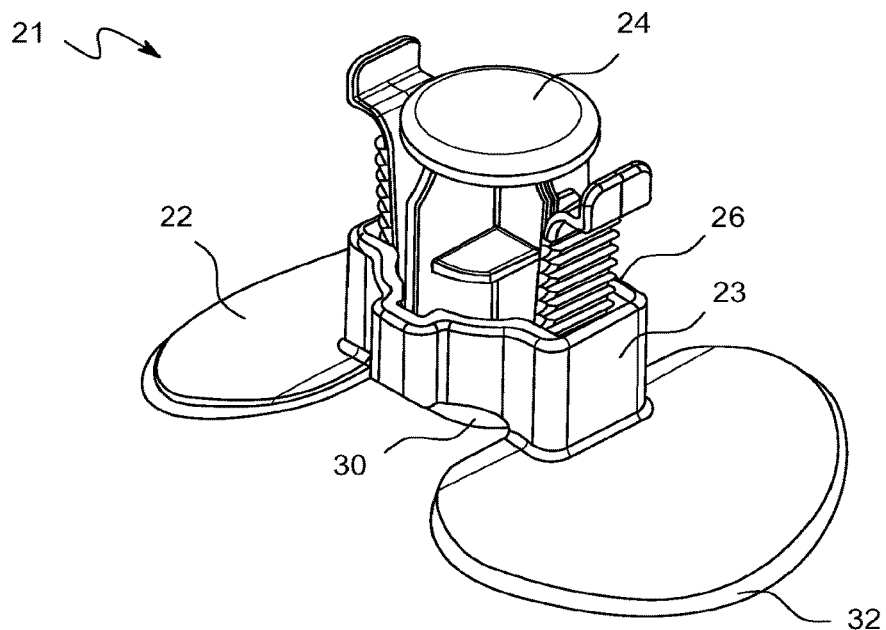
FIG. 10 illustrates a fourth exemplary embodiment of a hemostasis device for use with an adhesive pad according to the present invention.
Figures 11A, 11B:
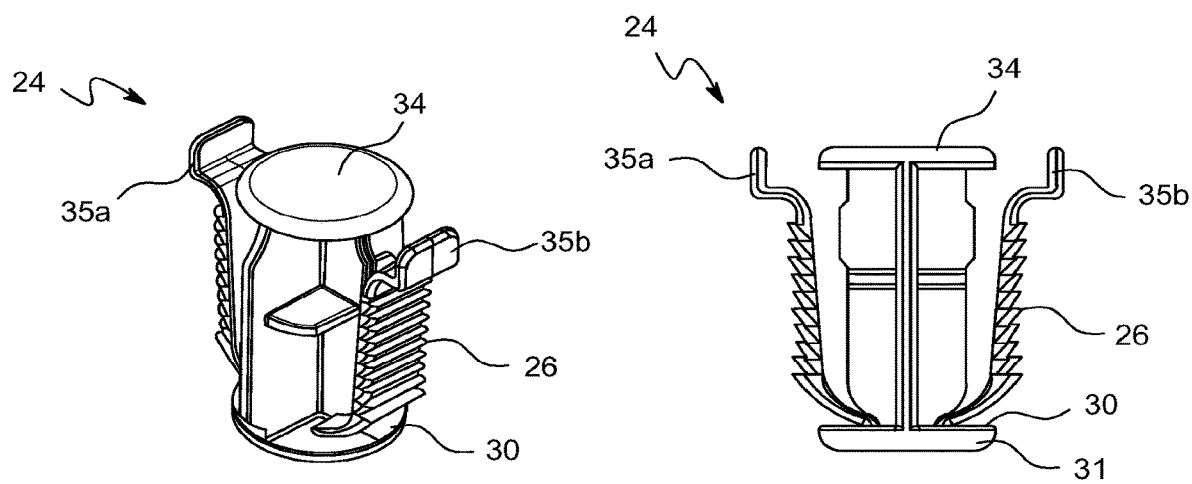
FIGS. 11A and 11B illustrate an exemplary plunger for use in the hemostasis device of FIG. 10.
Figure 12:
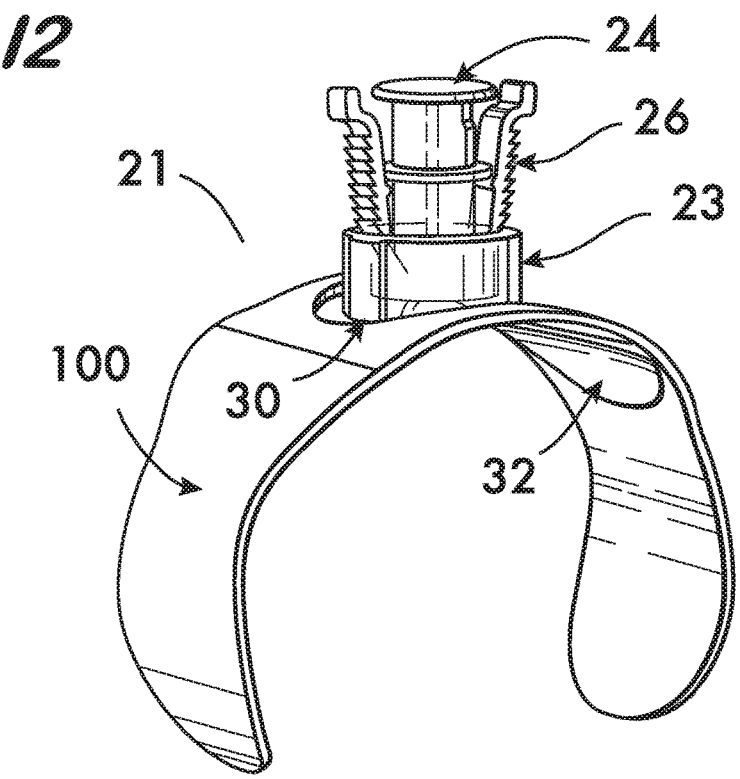
FIG. 12 illustrates a perspective view of an exemplary embodiment of a hemostasis system for adhering to a patient's skin and applying a compressive force to a puncture site.
Figure 13:
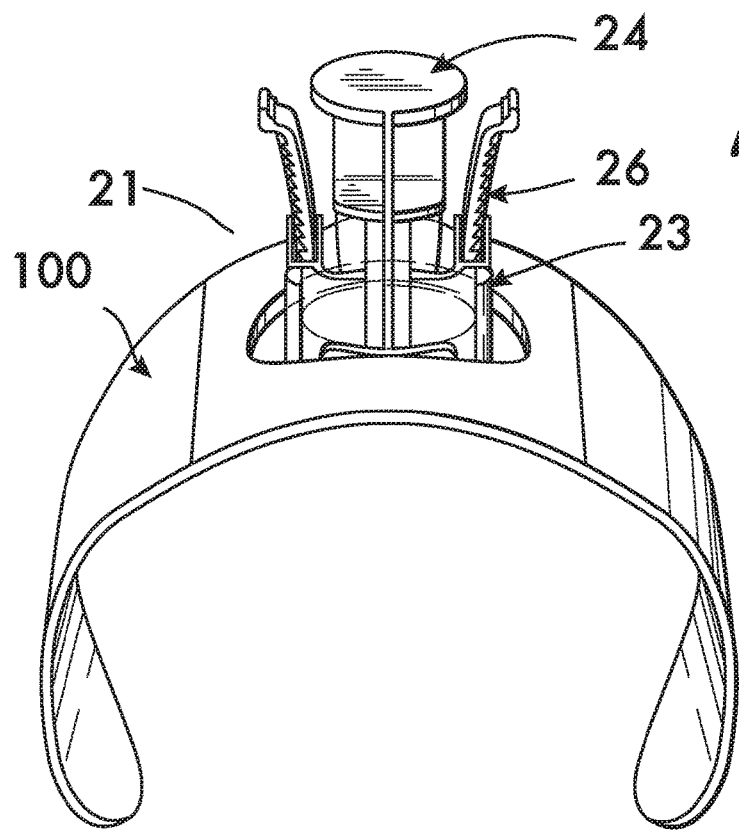
FIG. 13 illustrates a side perspective view of the hemostasis system of FIG. 12.
Figure 14:
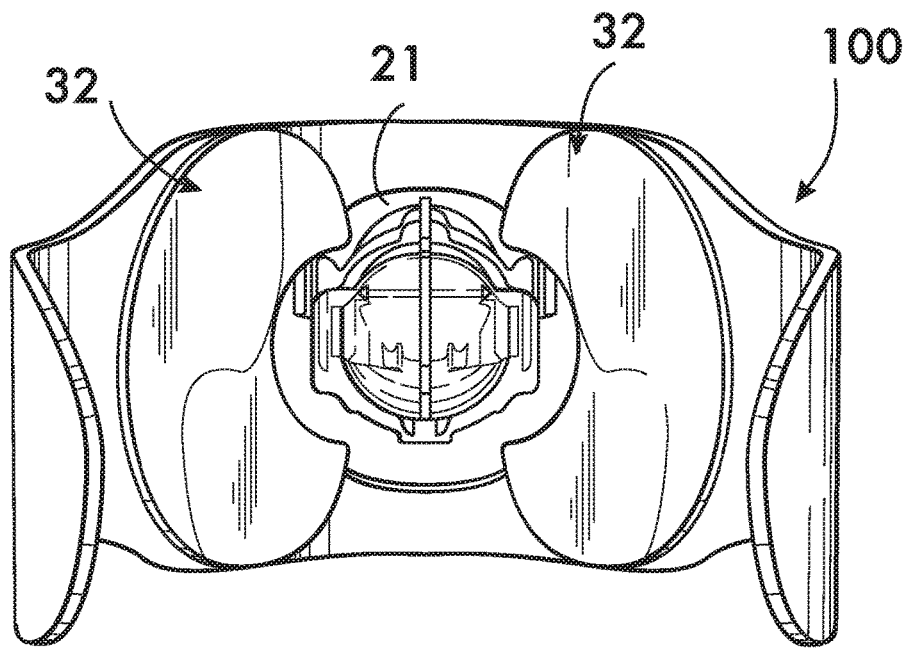
FIG. 14 illustrates a bottom view of the hemostasis system of FIG. 12.
Figure 15:
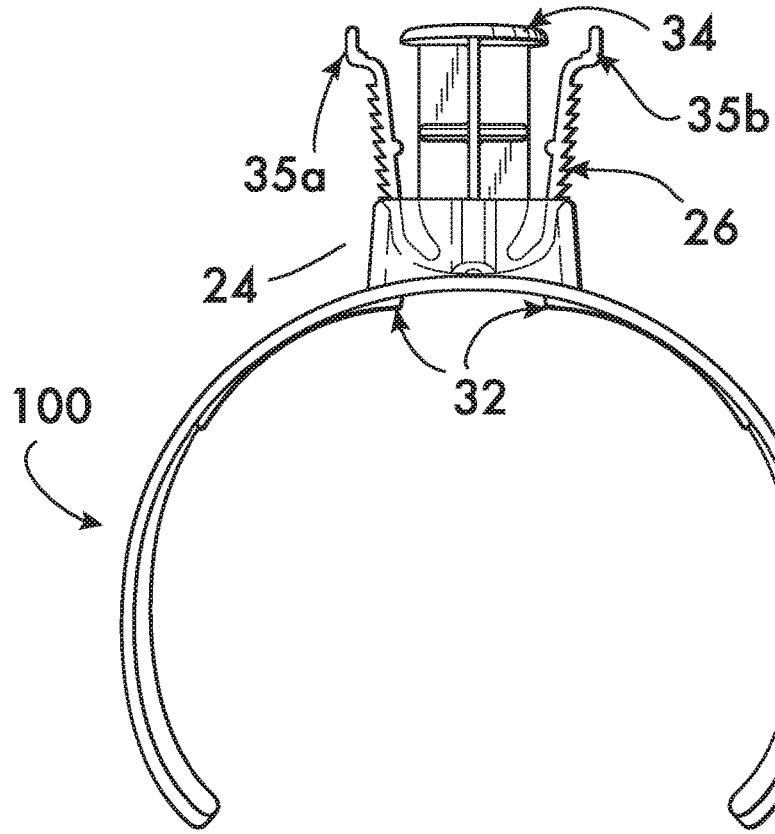
FIG. 15 illustrates a side view of the hemostasis system of FIG. 12.

FIGS. 10, 11A and 11B illustrate another embodiment of the hemostasis device. Like hemostasis device 1 shown in FIGS. 5-9, the hemostasis device 21 may comprise a footplate 22, a cylinder 23 centrally positioned on footplate 22, and a plunger 24. Though not shown in FIGS. 10, 11A and 11B, the footplate 22 may further include stabilizing means such as curved arms 5 as discussed above.

The engagement of the plunger 24 within the cylinder 23 provides for one-directional movement of the plunger 24 with respect to the cylinder 23 by use of a ratcheting mechanism. In the embodiment shown in FIGS. 10, 11A and 11B, a plurality of racks 26 attached to the plunger 24 may engage a corresponding pawl or rack (not shown) in the cylinder 23 in such manner as to limit the plunger 24 to movement downwardly in the cylinder 23. In other words, the plunger 24 may be forced downwardly toward the puncture site, but is restrained from movement upwardly in the cylinder 23 by the combination and position of racks 26 and the corresponding pawls or racks in the cylinder 23. In another embodiment, a single rack 26 is attached to the plunger 24 and may engage a corresponding pawl or rack in the cylinder 23. In yet another embodiment, one or more racks 26 positioned on the cylinder 23 may engage a pawl positioned on plunger 24 in such manner as to limit plunger 24 to movement downwardly in cylinder 23.

As shown in FIGS. 11A and 11B, the plunger 24 may include various components. For example, the plunger 24 may be designed and configured such that the plunger includes a central plunger portion 34 and wings 35a and 35b. The central plunger portion 34 may be configured to receive applied downward force as provided by the clinician. The wings 35a and 35b may include the racks 26 such that as the clinician applies force to the central plunger portion 34, the wings 35a and 35b ratchet downward against the racks 26 of the cylinder 23. The wings 35a and 35b may also provide a means for releasing the pressure being applied to the puncture site by the plunger 24. The wings 35a and 35b may be squeezed toward the central plunger portion 34, thereby disengaging the racks 26, allowing the plunger 24 to move away from the puncture site. This may be done when hemostasis is achieved or if too much pressure has been applied to the puncture site. Further, this embodiment permits one-handed movement of the plunger 24 from the puncture site by compression of wings 35a and 35b and movement of the plunger 24 through the cylinder 23 and away from the puncture site.

Similarly, the bottom of the plunger 24 may include a compression surface 30 having a compression pad 31 adhered thereto. The compression pad 31 may have a pro-coagulant coating such as calcium alginate, oxidized regenerated cellulose, seaweed extracts, a pro-coagulant polymer, another pro-coagulant coating, or combinations of two or more of these. The compression pad 31 may also have an antimicrobial coating such as silver or chlorhexidine.

One or more adhesive pads 32 having adhesive surfaces may be applied to the bottom of the footplate 22 such that, during operation, the pads 32 may adhere to the skin of the patient when the hemostasis device 21 is in use, thereby assisting in securing the footplate 22 to the patient's skin to prevent the hemostasis device from shifting position on the skin when in use. The size of the pads 32 may be determined relative to the pressure being applied by the hemostasis device 21 to the puncture site and/or the part of the body to which the hemostasis device 21 is being applied. The size of the pads may also be determined relative to the type of adhesive being used on the pads. For example, the pulling force exerted on the patient's skin by the one or more pads 32 should be greater than the compressive force applied on the puncture site by the plunger 24. Higher compressive forces applied on the puncture site may be achieved by increasing the surface area of the pads 32 that are in contact with the skin, either by increasing the size and/or number of pads 32, using an adhesive having greater adhesive strength, or a combination of the two. Typical temporary medical adhesives may be used such that when hemostasis is achieved, the hemostasis device 21 is easily removed.

It should be noted that the hemostasis devices as shown in FIGS. 5-11B are shown by way of example only. Additional design features may be incorporated. For example, although only a ratcheting mechanism is disclosed herein to permit only unidirectional movement of plunger, additional locking mechanisms such as a screw machine (not shown herein) or other similar mechanisms may be employed.

The method for applying a compressive force to a patient's skin at a puncture site using the hemostasis devices as shown in FIGS. 5-9 will now be described. In practice, after the removal of the needle from the puncture site in a patient's arm, the hemostasis device 1 may be positioned over the puncture site, the apertures 14 in the footplate 2 permitting visual observance by the medical technician to insure that the compression surface 10 of the plunger 4 and compression pad 11 adhered thereto are placed over the puncture site. In practice, after the removal of the needle from the puncture site in a patient's arm, the hemostasis device 1 may be positioned over the puncture site. In certain embodiments, adhesive pads 12 are positioned on the bottom surface of the footplate 2. There may also be one or more apertures 14 in the footplate 2 permitting visual observance by the clinician to insure the proper positioning of the compression surface 10 of the plunger 4 (and, optionally, a compression pad 11) over the puncture site. A compressive force is then applied to the puncture site by advancing the plunger 4 through the receiving device 3, and the motion restricting components are engaged to prevent reverse movement of the plunger 4.

The adhesive pads 12 may securely hold the hemostasis device in position on the skin. A finger of the clinician may be placed on the arcuate elements 9 of the plunger 4. A second finger of the clinician may be placed in engagement with one of the curved arms 5 as a third finger of the clinician may be placed in engagement with the other of the curved arms 5. The first finger may be used to force down the plunger 4 until the compression surface 10 (and, optionally, the compression pad 11 firmly bears against the puncture site, the second and third fingers of the clinician in clamping engagement with the curved arms 5 holding the hemostasis device 1 firmly in position until hemostasis is achieved. Because the plunger 4 is prevented from moving away from the puncture site due to the ratcheting effect between the cylinder 3 and the plunger 4, the first finger of the clinician may be removed from the arcuate elements 9 of the plunger 4. Similarly, as adhesive pads 12 may hold the hemostasis device 1 to the skin of the patient, the clinician may remove their second and third fingers as well, leaving the hemostasis device 1 temporarily adhered to the patient's skin such that the plunger 4 maintains pressure on the puncture site.

After hemostasis has been achieved, the hemostasis device 1 may be removed from the skin of the patient, and a surgical dressing may then be applied to the site of the puncture site.

Figure 8:
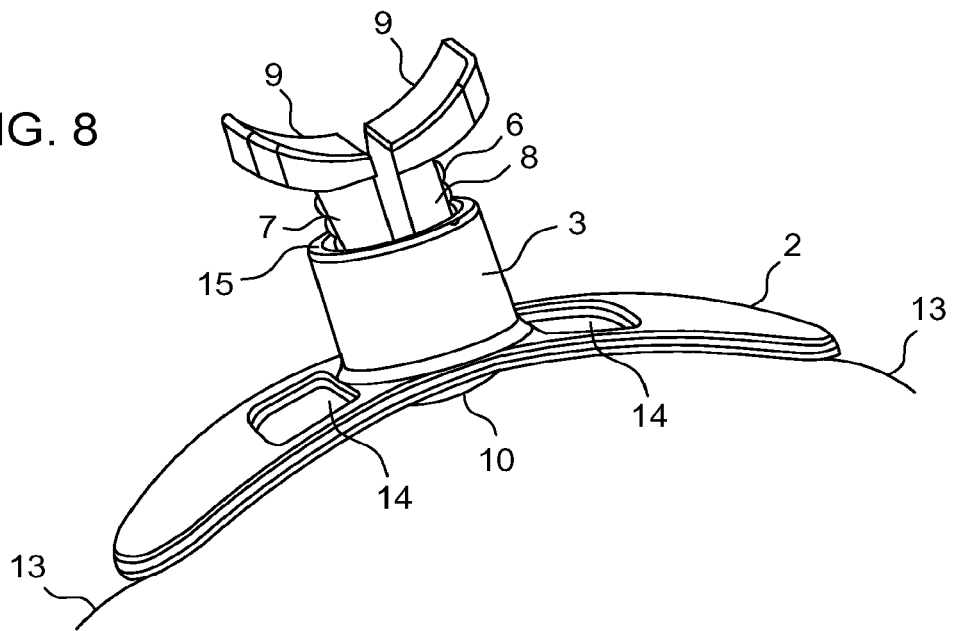
FIG. 8 illustrates a second exemplary embodiment of a hemostasis device for use with an adhesive pad according to the present invention.

In the embodiment shown in FIG. 8, the curved arms have been dispensed with. Two fingers, for example the thumb and middle finger of the clinician, may engage the cylinder 3 on opposite sides thereof and function just as they did in the embodiment of FIGS. 5-7.

In the embodiment of the hemostasis device shown in FIG. 9, only one curved arm 5 is employed. Two fingers, for example the thumb and middle finger of the clinician, may engage curved arm 5 and the side of cylinder 3 opposite the curved arm 5. In this embodiment, the thumb and middle finger of the clinician function just as they did in the embodiment shown in FIGS. 5-7.

The method as discussed above for operating hemostasis device 1 is applicable as well to hemostasis device 21 as shown in FIGS. 10, 11A, and 11B. The hemostasis device 21 is placed on the skin of a patient about a puncture site and adhered to the skin via one or more adhesive pads 32. The plunger 24 is then pressed downward through the cylinder 23 toward the puncture site until appropriate pressure has been applied to the puncture site by the compression pad 31. The hemostasis device 21 is then left in position, thereby allowing the medical technician operating the device to perform other tasks until hemostasis is achieved.

In another aspect of the invention, one embodiment of the hemostasis system of the present invention is shown in FIGS. 12-15. As shown in FIGS. 12-15, the adhesive pad 100 overlies the hemostasis device 21 so that the opening 112 in the central portion 110 of the adhesive pad 100 is positioned coincident with the cylinder 23 of the hemostasis device 21 and the first and second side portions 114 and 116 are adhered to the top surface of the footplate 22 and to the patient's skin proximal to the footplate 22.

In embodiments of the hemostasis system employing hemostasis devices such as shown in FIGS. 5-7, the hemostasis device is operated as described above. The adhesive pad 100 overlies the hemostasis device so that the opening 112 in the central portion 110 of the adhesive pad 100 is positioned coincident with the cylinder of the hemostasis device and the first and second side portions 114 and 116 are adhered to the top surface of the footplate and to the patient's skin proximal to the footplate. As the adhesive pad 100 secures the hemostasis device to the skin of the patient, the clinician may remove their second and third fingers as well, leaving the device temporarily adhered to the patient's skin such that the plunger maintains pressure on the puncture site. After hemostasis has been achieved, the hemostasis system may be removed from the skin of the patient, and a surgical dressing may then be applied to the site of the puncture.

In embodiments of the hemostasis system employing a hemostasis device such as shown in FIG. 8, the curved arms have been dispensed with. Two fingers, for example the thumb and middle finger of the clinician, may engage the cylinder on opposite sides thereof and function just as they did in the embodiment of FIGS. 5-7.

In embodiments of the hemostasis system employing a hemostasis device as shown in FIGS. 10, 11a and 11b, the hemostasis device is operated as described above. As shown in FIGS. 12-15, the adhesive pad 100 overlies the hemostasis device 21 so that the opening 112 in the central portion 110 of the adhesive pad 100 is positioned coincident with the cylinder 23 of the hemostasis device 21 and the first and second side portions 114 and 116 are adhered to and extend beyond the top surface of the footplate 22.

The method as discussed above for applying a compressive force to a patient's skin at a puncture site may employ the hemostasis system such as shown in FIGS. 12-15. The hemostasis device 21 is placed on the patient's skin at a puncture site. The release layer 106 of the adhesive pad 100 is removed, and the adhesive pad 100 is then placed over the hemostasis device 21 so that the opening 112 in the central portion 110 of the adhesive pad 100 is positioned coincident with the cylinder 23, and the first and second side portions 114 and 116 are adhered to the top surface of the footplate 22 and to the patient's skin proximal to the footplate. The plunger 24 is then pressed downward through the cylinder 23 toward the puncture site until appropriate pressure has been applied to the puncture site. The hemostasis device 21 is then left in position, thereby allowing the clinician operating the device to perform other tasks until hemostasis is achieved. After hemostasis has been achieved, the hemostasis system may be removed from the skin of the patient, and a surgical dressing may then be applied to the site of the puncture.

It should be noted that the configurations and mechanisms discussed above are shown by way of example only. Additional configurations and mechanisms may be used to implement a hemostasis system. For example, a compressive force may be applied directly to the footplate. As above, the footplate may be adhered directly to a patient's skin proximal a puncture site. An inflatable bladder or other mechanical expander may be positioned between the footplate and the puncture site or between the footplate and a second plate positioned on the side of the footplate distal to the puncture site and attached to the footplate only at each end such that the bladder is positioned between the footplate and the second plate. The bladder or other mechanical expander may then be inflated, exerting a force against the footplate and thus providing a compressive force against the puncture site. Once hemostasis is achieved, the bladder or other mechanical expander may be deactivated and the footplate removed from the patient's skin. Examples of alternative mechanical expanders that may also be used include spring-loaded and threaded expanding devices.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments. Thus, this disclosure is not limited to the particular systems, devices, and methods described, as these may vary.

The terminology used in the description is for the purpose of describing the particular versions or embodiments only, and is not intended to limit the scope. As used in this document, the singular forms "a," "an," and "the" include plural references unless the context clearly dictates otherwise. Unless defined otherwise, all terms used herein have the same meanings as commonly understood by one of ordinary skill in the art.

As various changes could be made in the above articles and methods without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the invention as disclosed herein. It is intended that the specification be considered exemplary only, with the scope and spirit of the invention being indicated by the claims. The appended claims are intended to be construed to include all such embodiments and equivalent variations.

What is claimed is:

1. A hemostasis system for adhering to a patient's skin and applying a compressive force to a puncture site, the hemostasis system comprising:
    (a) a hemostasis device comprising:
        a footplate having a top surface and a bottom surface,
        a receiving device positioned on the footplate, a
            plunger positioned within the receiving device and configured to move therethrough and apply a compressive force to the patient's skin at the puncture site, and a plurality of motion restricting components interposed between the receiving device and the plunger to restrict reverse movement of the plunger through the receiving device; and (b) an anchoring adhesive pad comprising a flexible backing layer with a bottom surface, a first side portion, a second side portion, and a central portion;

an adhesive layer on the bottom surface of the backing layer; and a release liner removably secured to the adhesive layer;

wherein the central portion defines a hole sized to receive the receiving device, and wherein the first side portion and the second side portion of the backing layer overlay and adhere to the top surface of the footplate of the hemostasis device and extend beyond the footplate to the patient's skin.

2. The hemostasis system of claim 1, wherein the backing layer of the anchoring adhesive pad comprises paper, woven fabric, or non-woven plastic film.

3. The hemostasis system of claim 1, wherein the backing layer of the anchoring adhesive pad comprises a non-woven plastic film.

4. The hemostasis system of claim 3, wherein the non-woven plastic film is selected from the group consisting of polyethylene, polypropylene, polyurethane, polyester, poly(ethylene-vinyl acetate), and poly(vinyl chloride).

5. The hemostasis system of claim 1, wherein the release liner of the anchoring adhesive pad has an opening coincident with the opening in the central portion of the backing layer.

6. The hemostasis system of claim 1, wherein the release liner of the anchoring adhesive pad comprises a plurality of separate sections.

7. The hemostasis system of claim 1, wherein the release liner of the anchoring adhesive pad is paper.

8. The hemostasis system of claim 1, wherein the plunger of the hemostasis device further comprises a compression pad.

9. A method for applying a compressive force to a patient's skin at the site of a puncture site, the method comprising the steps of:

providing an anchoring adhesive pad configured to be received by a hemostasis device comprising a footplate having a top surface and a bottom surface, a receiving device positioned on the footplate, a plunger positioned within the receiving device and configured to move therethrough, and a plurality of motion restricting components interposed between the receiving device and the plunger to restrict reverse movement of the plunger through the receiving device wherein the anchoring adhesive pad comprises a flexible backing layer having a bottom surface, a first side portion, a second side portion, a central portion positioned between the first side portion and the second side portion, defining an opening to receive the receiving device, and an adhesive layer applied to the bottom surface of the flexible backing layer, wherein the first side portion and the second side portion of the backing layer overlay and adhere to the top surface of the footplate of the hemostasis device and extend beyond the footplate to the patient's skin proximal to the puncture site; and improving securement of the hemostasis device at a puncture site.

10. The method of claim 9, further comprising improving a compression force of the hemostasis device at the puncture site.

11. A kit comprising:

(a) a hemostasis system comprising:

a hemostasis device comprising a footplate having a top surface and a bottom surface, a receiving device positioned on the footplate, a plunger positioned within the receiving device and configured to move therethrough and apply a compressive force to the patient's skin at the puncture site, and a plurality of motion restricting components interposed between the receiving device and the plunger to restrict reverse movement of the plunger through the receiving device; and (b) an anchoring adhesive pad comprising a flexible backing layer with a bottom surface, first side portion, a second side portion, a central portion positioned between the first side portion and the second side portion, defining an opening to receive the receiving device;

an adhesive layer applied to the bottom surface of the backing layer; and a release liner removably secured to the adhesive layer;

wherein the first side portion and the second side portion of the backing layer overlay and adhere to the top surface of the footplate of the hemostasis device and extend beyond the footplate to the patient's' skin proximal to the puncture site.

* * * * *